(12) United States Patent
Tanabe et al.

(10) Patent No.: US 6,949,383 B2
(45) Date of Patent: Sep. 27, 2005

(54) MUTAGENESIS METHOD

(75) Inventors: Kiyoshi Tanabe, Toyama (JP); Mitsuru Furusawa, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/600,027

(22) PCT Filed: Nov. 11, 1999

(86) PCT No.: PCT/JP99/06294

§ 371 (c)(1),
(2), (4) Date: Sep. 6, 2000

(87) PCT Pub. No.: WO00/28015

PCT Pub. Date: May 18, 2000

(65) Prior Publication Data

US 2003/0124725 A1 Jul. 3, 2003

(30) Foreign Application Priority Data

Nov. 11, 1998 (JP) .......................................... 10/321143

(51) Int. Cl.[7] .......................... C12N 15/01; C12N 1/20
(52) U.S. Cl. ................................... 435/440; 435/252.8
(58) Field of Search .............................. 435/440, 252.8, 435/243, 471; 536/23.1

(56) References Cited

U.S. PATENT DOCUMENTS 5,348,872 A  *  9/1994  Lin et al.
5,928,866 A  *  7/1999  Imamoto et al.

OTHER PUBLICATIONS

Pan et al. Involvement of Topoismerase IV and DNA Gyrase as Ciporfloxacin Targets in Streptococcus pneumoniae Antimicrobioal Agents and Chemotherapy Oct. 1996, P. 2321–2326.*

Fijakowska et al. Unequal fidelity of leading strand and lagging strand DNA replication on the *Escherichia coli* chromosome vol. 95, pp. 10020–10025, Aug. 1998.*

Iwaki et al. Preferential replication–dependent mutagenesis in the lagging DNA strand in *escherchia coli* mol gen genct 1996 251: 657–664.*

Garza et al. Moltility proteinn interactions in the bacterial flagellar motor vol. 92 pp. 1970–1974 Mar. 1995.*

Susset et al. Separation of transcriptional activation and silencing functions of the RAP1–encoded repressor/activator protein 1: Isolation of viable mutants affecting both silencing and telomere length vol. 88 pp. 7749–7753 Sep. 1991.*

Ota et al. A gene encoding a putative tyrosdine phosphatase suppresses lethality of an N–end rule–dependent mutant vol. 89, pp. 2355–2359 Mar. 1992.*

Herbst et al. A mutation in robosomal protein L9 affects ribosomal hopping during translation of gene 60 from bacteriophage T4 vol. 91 pp. 12525–12529 Dec. 1994.*

* cited by examiner

*Primary Examiner*—Terry McKelvey
*Assistant Examiner*—Nancy T. Vogel
(74) *Attorney, Agent, or Firm*—Wenderoth, Lind & Ponack, L.L.P.

(57) ABSTRACT

This application provides a method for mutagenesis of a gene, which comprises introducing much more point mutations into one strand of double-stranded genomic DNA of cell or organism individual than into another strand. In accordance with such a method, it is now possible to efficiently and effectively construct various useful mutants of microorganisms, cells or organism individuals. It is also now possible by analyzing the mutating conditions of the gene to clarify the mechanism of drug resistance, to estimate the occurrence of a novel insensible microorganism or to develop a drug therefor, to analyze the mutation of an oncogene and the mechanisms of cancer metastasis and increase in malignancy, to develop a therapeutic method using these mechanisms, etc.

5 Claims, 8 Drawing Sheets

SEQUENCE LISTING

```
<160> NUMBER OF SEQ ID NOS:  5

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 1
aagcggggta attgtgcgat gcacaatatc gttgatttgt tgagggcac cccccccc          59

<210> SEQ ID NO 2
<211> LENGTH: 57
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 2
ttgtgcatcg cacaattacc ccgcttatag agcaacaaaa gatcccgccc ccccccc          57

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 3
gattaggatc cactaatatc gggggggggg                                       30

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 4
```

-continued

```
ggatcttttg ttgctctata a                                        21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 5
tgcccctcaa caaatcaacg a                                        21
```

MUTAGENESIS METHOD

BACKGROUND OF THE INVENTION

1. Field of the Invention

The invention of this application relates to an effective and highly efficient method for introducing a random mutation in which mutation can be efficiently introduced into a cell or an organism individual and also a risk of extinction of treated cell or individual groups can be reduced, and this invention also relates to mutants and mutated phenotypic gene obtained by the said method.

2. Description of the Related Art

With regard to an art for a genetic modification of cells or organism individuals, a method where mutagen such as ultraviolet ray, radioactive ray or mutagenic substance is applied to cells or organism individuals, a method where exogenous gene is introduced into cells or organism individuals to modify by means of genetic engineering, etc. are available. In the case of induction of mutation in specific gene, there has been known a method where genetic engineering means such as site-specific mutation induction and in vitro mutation induction by accumulation of replication mistake in DNA utilizing a PCR amplifying technique.

Generally, when the site into which gene or mutation to be modified is clear, genetic engineering means may be sometimes effective while, when the knowledge about the phenotype to be modified or gene therefor is insufficient, there is an effective method utilizing a random mutation induction where mutation is randomly introduced into gene and, from the resulting mutant, cells or organism individuals having the desired mutation phenotype is selected. In inducing the random mutation, a method where mutation is induced by irradiation of ultraviolet ray, X-ray or radioactive ray to cells or organism individuals, a method where mutation is induced by treating with a mutagenic substance such as nitrogen mustard or nitrosoguanidine, and the like are available.

In the conventional art for introducing a random mutation, the mutation rate induced by ultraviolet ray or mutagen has an important influence on efficiency and effect of the treatment. Thus, when the induced mutation rate is within an optimum range, mutation in a sufficient amount for DNA is accumulated while, when it is less than the optimum amount, mutation may be sometimes repaired by a repairing mechanism, etc. of DNA whereby mutation cannot be introduced efficiently. Further, when it is more than the optimum amount, the lethal effect to the organism by the introduced mutation becomes strong whereupon, before the desired mutant is obtained, the group into which mutation is introduced and is treated therewith dies out resulting in no production of the desired mutant.

The same thing may be said for the optimum amount not only just for one treatment but also for plural and continued treatments where mutagenetic treatment and mutant selection are carried out one after another in order to obtain more highly useful mutant. Thus, unless the optimum amount is determined carefully, the efficiency is bad or the group subjected to a mutagenesis dies out whereby it is at last impossible to obtain a highly useful mutant. In addition, there may be a case where it is necessary to introduce plural mutations into a gene in which phenotype of cells or organism individuals to be modified by a random introduction of mutation is single or a case where it is necessary to introduce mutation into plural genes and, in such cases, randommutation is to be inserted until preferred mutation is accumulated in such genes. However, accumulation of many mutations results in a high risk where lethal mutation is introduced into the gene which is necessary for living. Thus, the higher the mutation rate, the more the risk of extinction of the treated cells or organism individuals whereby it cannot be expected to obtain a useful mutant in an efficient manner.

In recent years, although the object is not to genetically modify the cells or the organism individuals, a method has been developed for an efficient introduction of a random mutation into gene inserted into a plasmid in the following mutant of *Escherichia coli* utilizing the fact that the mutation rate of *E. coli* simultaneously having mutD, muS and mutT (which are mutator genes concerning proofreading mechanism of mispair of DNA base pair, A/T-G/C transversion and mismatch repair of DNA, respectively) is 5,000-fold of a wild type strain (Molecular Biotechnology, 7:189–195, 1997). According to such a method, it is possible to introduce a mutation for each 1,000 base pairs into genes on plasmid by incubation for 24 generations within about one day. However, although such a high mutation rate increases the probability of mutagenesis of gene into which mutation is to be introduced, that also increases a risk of introduction of mutation into other genes such as those necessary for living. Therefore, when the length of the DNA region into which mutation is to be introduced is 100 base pairs or less or when mutation is to be introduced into plural parts, a PCR is recommended because the above method is not practical due to an increase in numbers of growth generation. It has been also pointed out that, since the mutation rate is high, incubation of the strain for a long period causes an affection to the cell per se or genotype thereof whereby carefulness is required. Accordingly, although the said method is suitable for introduction of mutation into gene on plasmid introduced into a host, it is not suitable for a genetic modification of the host itself.

As mentioned above, in the conventional method for the introduction of a random mutation into cells or organism individuals, introduction of many mutations and avoidance of extinction of mutation-introduced group are in a relation of antinomy whereby it is difficult to obtain various and useful mutants in an efficient manner.

The invention of this application has been achieved in view of the above circumstances and its object is to provide a method where a random mutation is introduced into a cell or an organism individual in a high mutation rate and, at the same time, risk of extinction of treated group is reduced and useful and various mutants are efficiently obtained.

SUMMARY OF THE INVENTION

As an invention for solving the above-mentioned matters, this application provides a method for mutagenesis of a gene, which comprises introducing much more point mutations into one strand of double-stranded genomic DNA of cell or organism individual than into another strand.

The first preferred embodiment of the method of the present invention is that the point mutation is randomly introduced into four bases constituting the double-stranded genomic DNA.

The second preferred embodiment of the method of the present invention is that the cell or the organism individual is a mutant cell strain or a mutant organism individual having mutator gene in a mutation repair mechanism gene group. Incidentally, such a mutant cell strain or a mutant organism individual may inherently have the mutator gene or may be that into which extrinsic mutator gene is introduced.

The third preferred embodiment is that, in the above-mentioned method, the mutator gene is one or more mutator gene(s) selected from a group consisting of dnaQ, dnaE, mutL, mutS, mutH, uvrD and dam.

The fourth preferred embodiment of the above-mentioned method is that the mutator gene is a gene which causes a defect of mutation repair mechanism under a certain condition.

The fifth preferred embodiment of the method is that the condition for the defect of the mutation repair function is a certain temperature.

The sixth preferred embodiment of the method is that a step of introduction of mutation into genomic DNA under a certain condition and a step of selection of mutant under a selected pressure condition without introduction of mutation are repeated.

The seventh preferred embodiment of the method is that the step of introduction of mutation at the second time and thereafter are carried out under the same selected pressure as that in the step of mutant selection immediately therebefore.

As another invention, this application also provides a mutant of cell or organism individual where mutation is introduced into genomic DNA by any of the above-mentioned methods, and also provides a mutated gene which is isolated from the said mutant.

DESCRIPTION OF THE PREFERRED EMBODIMENTS

Figure 1:
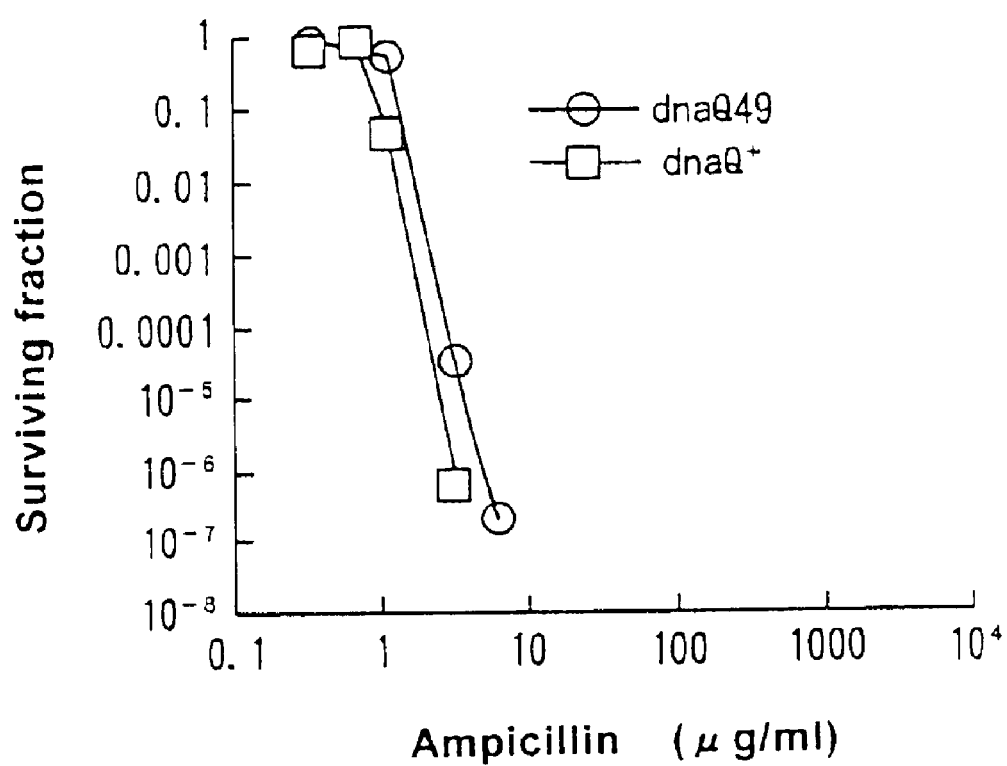
FIG. 1 is ampicillin concentration-survival curve of dnaQ49 strain before introduction of mutation and a wild type.

Natural mutation is fixed according to the following particulars. First, injury is generated by oxygen radicals or intravital metabolites which physically or chemically affect the chromosomal DNA or erroneous base pair is resulted by an error or the like in DNA duplication. Injury and duplication error resulted in chromosomal DNA as such are called promutagenic injury and, when the promutagenic injury is not repaired during the next DNA duplication, it is fixed in the chromosomal DNA as mutation. Most of the causes of generation of promutagenic injury in natural mutation are duplication error while the ratio of injury of chromosomal DNA affected by physical and chemical causes is small (CRC, 1(3):140–148, 1992). Duplication error is resulted by formation of erroneous base pair depending upon tautomerism of four kinds of base pairs during the DNA synthesis and its frequency is from $10^{-4}$ to $10^{-5}$ (Molecular Biology of the Cell, Garland Publish Inc., New York & London, 224–225, 1983) On the other hand, there are various mutation repair functions in cells whereby, due to mismatch repair system and proofreading function of DNA synthesizing enzyme, etc., the promutagenic injury is repaired to an extent of about $10^{-3}$ each and, finally, the frequency of fixation of the point mutation by a base substitution lowers to an extent of $10^{-10}$ to $10^{-11}$ per base (CRC, 1(3):140–148, 1992). Besides the above, there is a frameshift mutation by insertion and deletion of bases but its frequency is very little.

In the conventional random mutagenesis treatment, promutagenic injury is increased in chromosomal DNA by enhancing physical and chemical affection by energy rays such as radioactive ray and ultraviolet ray or by treatment with mutagen so as to increase the probability of fixation of the said mutation. Each of the type of mutagen and the promutagenic injury induced thereby has a characteristic feature and it is said that, for example, in the case of ultraviolet ray, both pointmutation and deletion mutation take place to the same extent while, in the case of point mutation, transition mutation in the direction of G/C-A/T often occurs. In addition, in the case of X-ray, there are a single strand break where only one of double strands of the DNA chains is cleaved and a double strand break where both are cleaved and, as a result, point mutation and deletion mutation occur where a deletion mutation is apt to take place as much as ten-fold as compared with a point mutation (Bunshi Hoshasen Seibutsugaku [Molecular Radioactive Biology] by Sohei Kondo, Tokyo University Press, 138–139, 1972).

On the other hand, in relation with the repair of mutation and duplication error, various mutator genes which increase the mutation have been known and they may be classified into five according to their functions (CRC, 1(3):140–148, 1992). The first one is mutation of α-subunit of DNA synthesizing enzyme concerning a control system for DNA duplication error. The thing which has been known up to now is dnaE gene and this mutator gene increases the mutation to an extent of 1,000- to 100,000-fold. The second one is mutation of ε-subunit of DNA synthesizing enzyme participating in proofreading function which instantly removes the mispair. With regard to this mutator gene, dnaQ (mutD) has been known and it also increases the mutation to an extent of 1,000- to 100,000-fold. The third one relates to a mismatch repair for removal and repair of mispair which was unable to be corrected by a proofreading function and mutL, mutS, mutH, uvrD, dam, mutY, mutM and ung have been known where each of them increases the mutation to an extent of 10- to 1,000-fold. The fourth one relates to a defecation function of a nucleotide pool used as a DNA material and mutT which increases only A/T-G/C transversion has been known. The cell having this mutator gene increases the GC content in DNA together with the growth of the cell and induces the mutation to an extent of 1,000- to 10,000-fold. To the last group belong mutA and mutC and they increase all types of transversion to an extent of about ten-fold although its function has not been known so well.

As such, the source for promutagenic injury which is a cause of mutation and the mutation which is induced thereby differ depending upon mutagens and it suggests the possibility that the resulting effect is different depending upon the type of mutagen which is used for the induction of a random mutation. In addition, in order to improve the effect of a random mutation, it is effective to randomly introduce a point mutation into all bases rather than to increase the frequency of transversion of specific base pair and frameshift mutation by insertion or deletion of a base.

The inventors of this application have carried out a simulation concerning the mutated numbers and distribution thereof in the case where mutation is uniformly introduced into both DNA strands of a double-stranded DNA (parity) and in the case where mutation is unequally accumulated on one of the DNA strands (disparity). The result shows that, under the condition where one mutation is introduced by one cleavage per genome (parity), a mode of the mutation numbers in distribution of mutation after ten generations is nearly ten in all of 12 simulations and the distribution is from 2 to 20 and that, when generation alternations are continued, the generation numbers are nearly in a mode of mutation numbers and the same distribution tends to be shifted. It has been on the other hand found that, under the condition where, although the total mutation rates are same, mutation is introduced into one strand of the double-stranded DNA in a probability of 100-fold or more as compared with another strand thereof (disparity), the mode of the mutation number mode after ten generations is 10 and its distribution is from 0 to 24. The above shows that, even when the total mutation numbers are same, distribution of mutation numbers is different after elapse of generations if many mutations are accumulated on one of the DNA strands (J. Theoretical Biology, 157:127–133, 1992).

Those findings by the inventors are important in introducing a random mutation. When energy ray such as radioactive ray or ultraviolet ray or mutagen is used as a cause for promutagenic injury, it is likely that a promutagenic injury is randomly induced to both strands of double-stranded DNA. Distribution of the mutated numbers in that case is same as that in the case of the above-mentioned parity. On the other hand, many of mutator genes participate in the function of repair of promutagenic injury and, therefore, distribution of the fixed mutated numbers as a result thereof is understood to be as follows. Since mutT relates to a base-specific repair function of A/T-G/C, mutation is in an increasing manner to GC base pairs. On the contrary, mutY, mutM and ung are in a reversed base dependency from mutT and, similarly, they are in an increasing manner to AT base pairs. Since dnaE and dnaQ participate in a proofreading function and a control of duplication error in lagging strand of a double-stranded DNA, they are DNA strand-dependent. Although mutL, mutS, mutH, uvrD and dam participate in a mismatch repair, they are not specific to DNA strands and, therefore, it is likely that they reflect the state of promutagenic injury. Similarly, mutA and mutC have no specificity to bases and DNA strands and participate in all types of transversion repair.

Incidentally, the actual effect of mutation is classified into that which has a lethal effect, that which is neutral having no or very little affection to gene functions, and that which gives certain changes to function. Generally, there is a possibility that the mutation showing no lethal effect is conserved. Further, with regard to randomicity of mutation, mutT, mutY, mutM and ung tend to increase the specific base pair when the function of mutator gene is taken into consideration. In addition, some mutagens increase a specific promutagenic injury such as formation of thymidine dimer. Mutagenesis of such a type is presumed to be insufficient for randomicity and, when that is used for mutagenesis, accumulation of specific mutation is resulted whereby there is a possibility that the effect of genetic improvement of organism is restricted.

On the other hand, in the synthesis of DNA, formation of erroneous base pair due to tautomerism of four kinds of bases takes place randomly for the four bases and, unless the promutagenic injury based thereupon is repaired, it is likely that a random mutation can be introduced into chromosomal DNA That which makes the above possible is mutator gene participating in a DNA proofreading function such as dnaE and dnaQ.

The inventors of this application have further found that, in the plasmid inserted into *Escherichia coli* having dnaQ which is a mutagenic mutator gene sensitive to temperature, lagging chain has a mutation rate of as high as several-fold to 100-fold as compared with leading chain after several duplications (Mol. Gen. Genet., 251:657–664, 1996). The inventors of this application have further found, as shown in Example 4, that more mutations are resulted in lagging chain than in leading chain even in genomic DNA of dnaQ49 strain. The fact that mutation is unequally accumulated in the double-stranded DNA is presumed to increase the diversity of mutation unlike in the case of uniform accumulation.

In order to effectively and efficiently introduce the mutation together with reducing the risk of extinction of cells or organism individuals, it is necessary that the genetic diversity of cells and organism individuals existing in the treating group is made much more and, for such a purpose, it is important that point mutations are unequally distributed in the double-stranded DNA together with a random introduction of the point mutations into four bases.

Based upon those findings, the inventors of this application have developed a method for preparing a mutant in efficient and effective manner in which more random point mutations are accumulated in one of DNA strands than in another strand so that the risk of extinction of mutated cells and organism individuals is reduced together with an increase in the mutation rate. To be more specific, mutator gene participating in a proofreading function is introduced into cells or organism individuals which are to be genetically modified or improved and a mutagenesis treatment is carried out under such a condition that random point mutations are accumulated in one of DNA strands in more amount than in another strand. It is also preferred to use a condition-expressing mutator gene such as temperature sensitivity as a mutator gene. When such a mutator gene is used, introduction of mutation and fixation of mutant can be freely set by means of operating the temperature condition, etc. The mutation rate to be induced is preferably within a range of 100- to 100,000-fold of natural mutation and the preferred condition is that one of DNA strands is accumulated with several fold to 100-fold or even more mutations than another strand is.

Incidentally, cells and organism individuals having mutator gene can be prepared by a known method (Journal of Bacteriology, 153, 1361–1367, 1983). It is also possible that the mutator gene is introduced by means of genetic engineering.

It is further possible that a step of introduction of mutation and a step of selection of mutant are carried out separately, the step of inducing the mutation is carried out under the condition where no selected pressure is applied, a step of fixation and selection of mutant is carried out after the treated individual group is proliferated to certain numbers and, in the second run and thereafter, the same operation is repeated so that the aimed mutant is prepared efficiently and effectively.

The invention of this application will now be illustrated by way of the following examples in more detail and in a specific manner although the present invention is not limited by the following examples.

EXAMPLE 1

HK 1366 (dnaQ49) strain and HK 1370 (dnaQ49) strain having temperature-sensitive mutator gene (dnaQ) (received from Professor Hisaji Maki, Nara Institute of Science and Technology) were incubated and degree of ampicillin resistance of each strain was measured.

Incidentally, in the dnaQ49 strain, ε-subunit of DNA polymerase III is mutated and there is a defect in a proof-reading function of DNA polymerase III. Therefore, DNA duplication error is not able to be proofread whereby mutation is generated in all base substitutions. Since such a mutation is sensitive to temperature, there is an increase in the mutation rate from $10^{-9}$ to $10^{-4}$ as a result of a shift of the incubation temperature from 24° C. to 37° C. On the other hand, a dnaQ+ strain is a strain where the ε-subunit of DNA polymerase becomes normal due to a reverse mutation of a dnaQ49 strain. This dnaQ+ strain was used as a wild type of the dnaQ49 strain (hereinafter, the dnaQ+ strain may be referred to as "wild type")

First, the wild type and dnaQ49 strain where no mutation was induced were planted on an agar medium containing ampicillin of various concentrations, incubated at 24° C. for two days to form colonies and ampicillin concentration-survival curves for dnaQ49 strain and wild type strain were prepared. Ampicillin sodium salt (Sigma, A-9518) was dissolved in pure water and the resulting original solution was added to a culture medium to give a desired diluted concentration. Preparation of the concentration-survival curve was carried out by measuring the absorbance of the medium at 550 nm.

The result is as shown in FIG. 1 and the dnaQ49 strain was found to have a slightly stronger ampicillin resistance than the wild type.

After that, each dnaQ49 strain and wild type was planted in a 5-ml L-broth medium in a density of 2,000 cells/ml and incubated for 24 hours at 37° C. which was a temperature for mutagenesis. Incidentally, in the case of the wild type, 1-methyl-3-nitro-1-nitrosoguanidine(MNNG; Aldrich 12,994-1) (one of the known mutagenic substances) was added to the medium in the concentrations of 0~60 µg/ml medium.

The grown cells were recovered after incubation for 24 hours and incubated at 24° C. for 48 hours in a medium of various ampicillin concentrations and the survival rate of each *Escherichia coli* was determined by a colony forming method.

Figure 2:
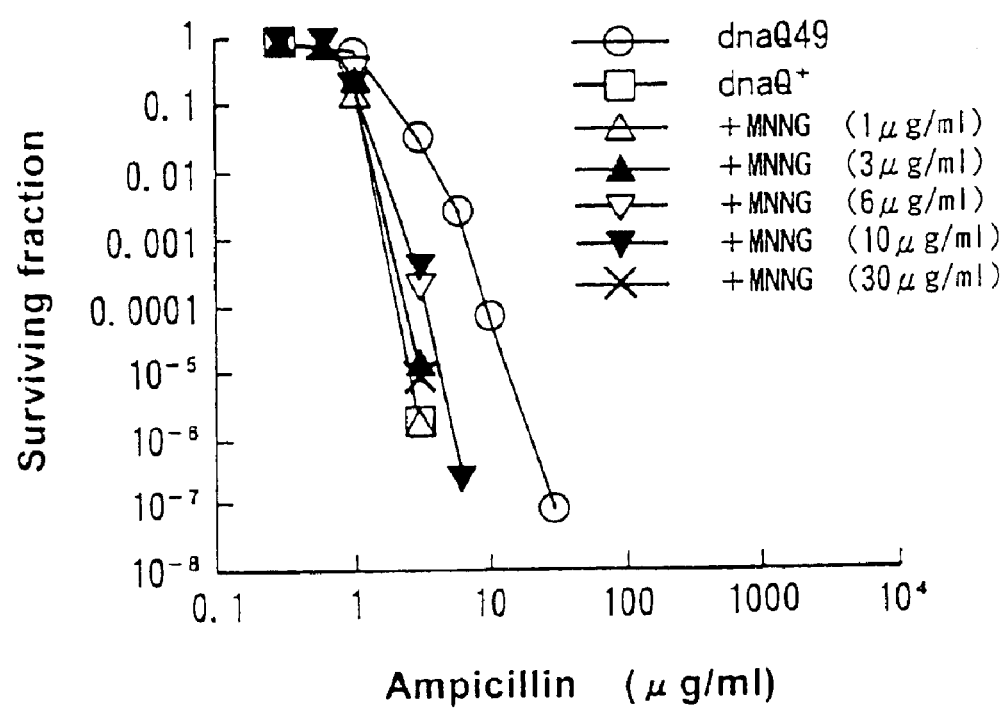
FIG. 2 is ampicillin concentration-survival curve showing ampicillin sensitivity of dnaQ49 strain after the first introduction of mutation, a wild type and an MNNG wild type.

FIG. 2 is ampicillin concentration-survival curve showing the ampicillin sensitivity of MNNG wild type, wild type and dnaQ49 strain mutated at 37° C. for 24 hours. The maximum concentration for ampicillin resistance of dnaQ49 strain was 30 µg/ml and was confirmed to be significantly higher than those of the wild type and the MNNG wild type (3~6 µg/ml). Incidentally, the wild type which was incubated in the presence of MNNG in the concentration of 60 µg/ml did not grow at all and, accordingly, it is believed that MNNG in a high concentration causes mutation even to the gene necessary for living whereby an extinction is resulted.

After that, the second mutagenesis was carried out using the colonies of the medium containing the maximum concentration of ampicillin grown in the above-mentioned incubation at 24° C. Thus, incubation was carried out at 24° C. in a medium containing 30 µg/ml of ampicillin for dnaQ49 strain, in a medium containing 6 µg/ml of ampicillin for a group treated with 10 µg/ml of MNNG, and in a medium containing 3 µg/ml of ampicillin for other MNNG-treated groups and the grown cells were washed, adjusted to a density of 2,000 cells/ml and incubated at 37° C. for 24 hours. Then, the cells were washed, planted in a medium containing various concentrations of ampicillin and incubated at 24° C. for 2–3 days to form colonies whereupon the survival rate of each *Escherichia coli* was determined. Incidentally, in the MNNG-treated group, the MNNG in the same concentration as in Example 2 was treated.

Figure 3:
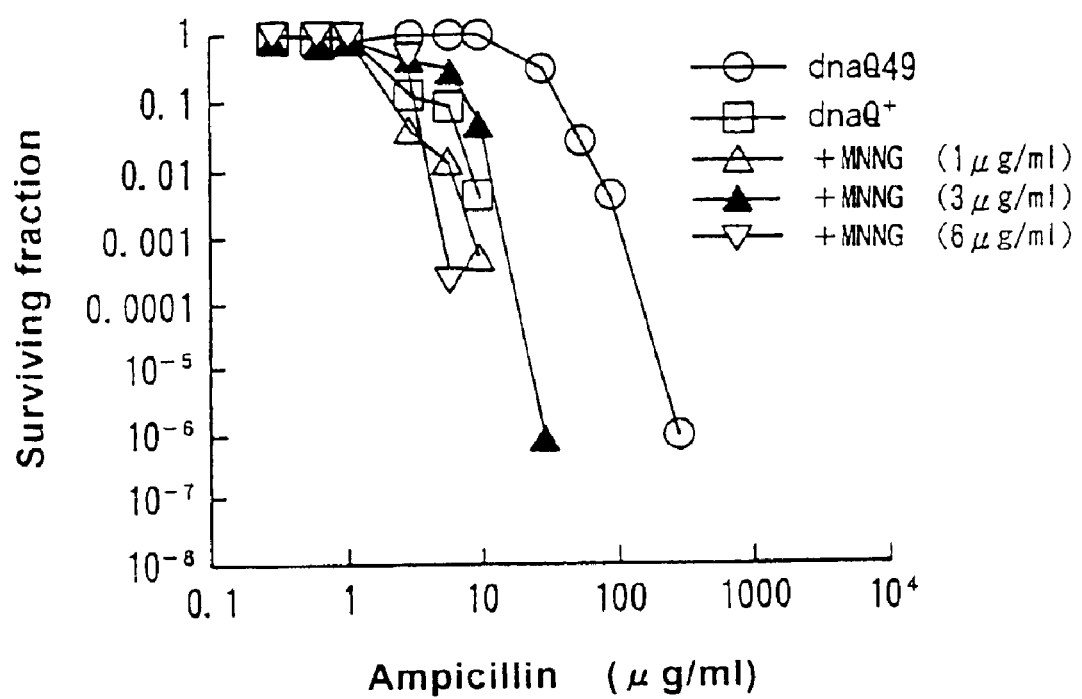
FIG. 3 is ampicillin concentration-survival curve showing ampicillin sensitivity of dnaQ49 strain after the second introduction of mutation, a wild type and an MNNG wild type.

FIG. 3 is ampicillin concentration-survival curve showing the ampicillin sensitivity of each MNNG treated group, wild type and dnaQ49 strain where the second mutagenesis was carried out. The maximum concentration for ampicillin resistance of dnaQ49 strain was 300 µg/ml and was confirmed to be significantly higher than those of the wild type and the MNNG wild type (6~30 µg/ml). Incidentally, the MNG-treated group which was not shown in FIG. 3 for the result shows that it died out.

Figure 4:
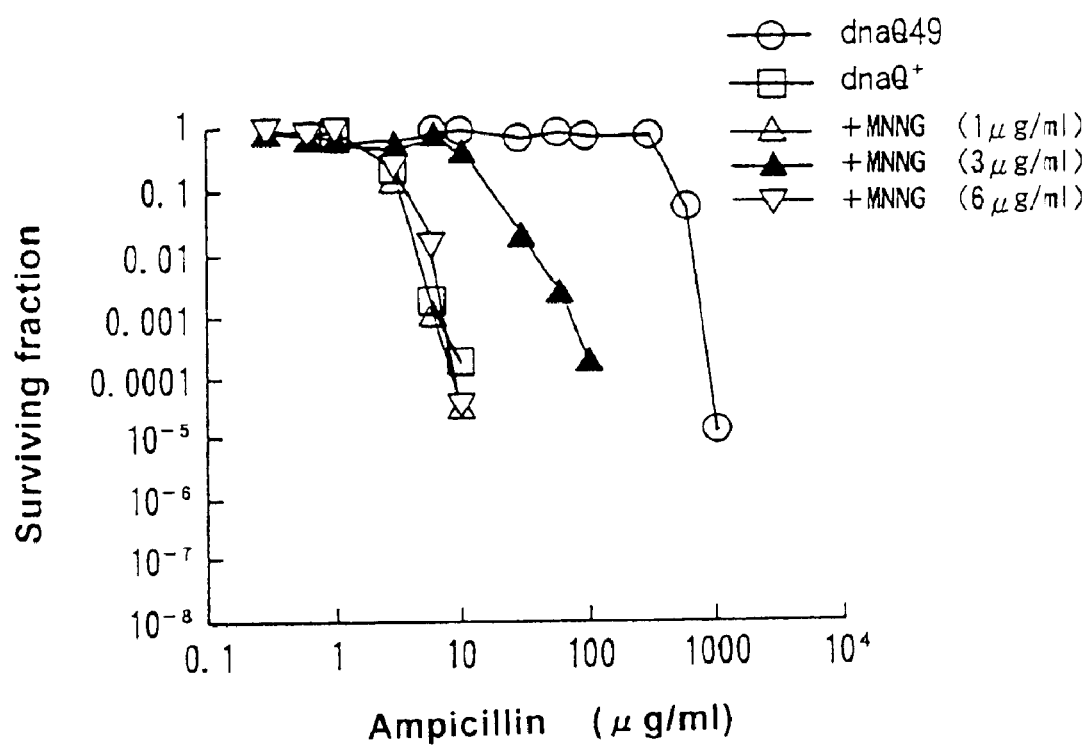
FIG. 4 is ampicillin concentration-survival curve showing ampicillin sensitivity of dnaQ49 strain after the third introduction of mutation, a wild type and an MNNG wild type.
Figure 5:
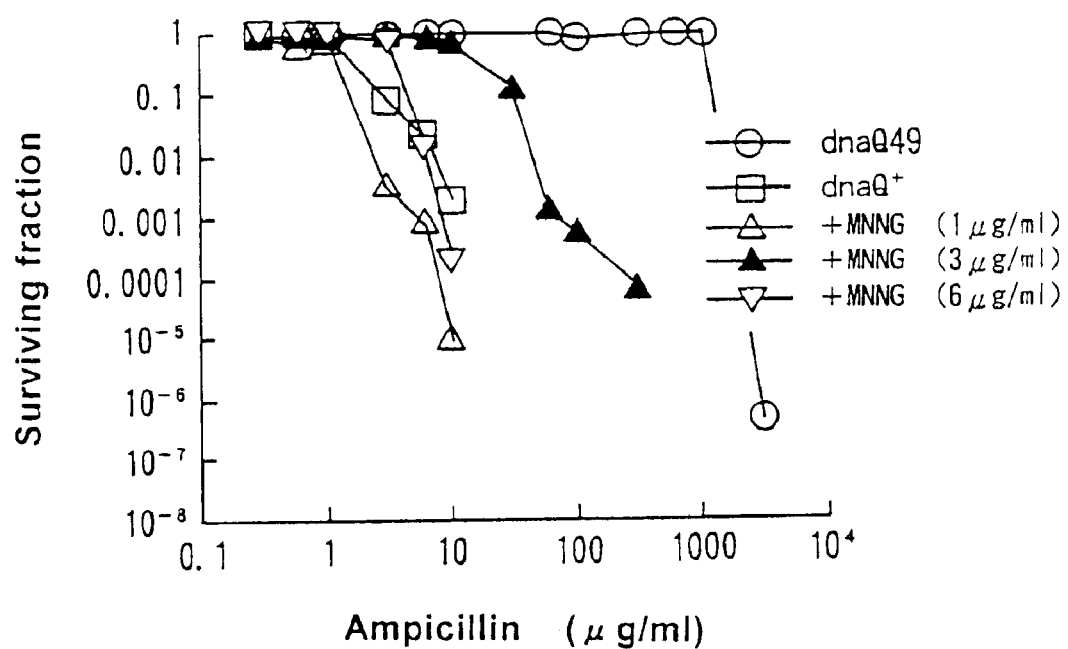
FIG. 5 is ampicillin concentration-survival curve showing ampicillin sensitivity of dnaQ49 strain after the fourth introduction of mutation, a wild type and an MNNG wild type.
Figure 6:
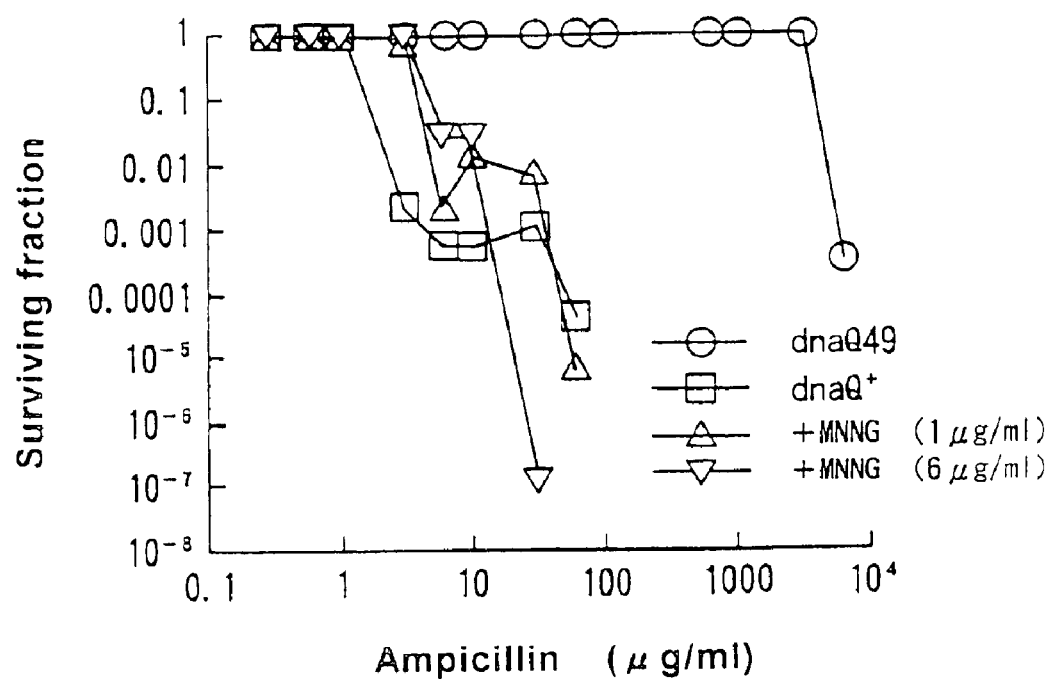
FIG. 6 is ampicillin concentration-survival curve showing ampicillin sensitivity of dnaQ49 strain after the fifth introduction of mutation, a wild type and an MNNG wild type.

After that, the same operation was repeated and mutagenesis was carried out up to the fifth run. The ampicillin concentration (maximum concentration for ampicillin resistance at the colony formation in the preceding stage) at the proliferation at 24° C. and the days for the colony formation at 24° C. are as shown in Table 1. FIGS. 4 to 6 are curves of ampicillin concentration vs. survival after mutagenesis of third to fifth runs.

Figure 7:
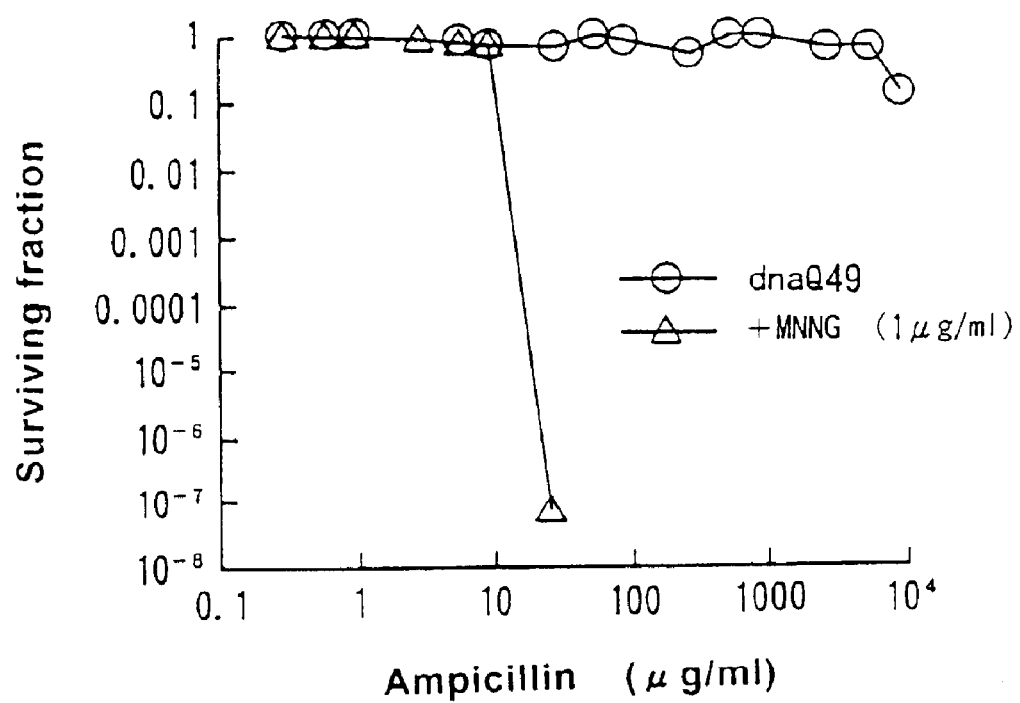
FIG. 7 is ampicillin concentration-survival curve showing ampicillin sensitivity of another dnaQ49 strain after the fifth introduction of mutation.

It is clear from those results that, by the mutagenesis treatment of up to the fifth run, dnaQ49 strain which grew even in the presence of about 6,000 µg/ml of ampicillin was obtained. When the same mutagenesis treatment was carried out in another dnaQ49 strain, an ampicillin resistant strain up to about 10,000g/ml was obtained by five mutagenesis treatments (FIG. 7). Incidentally, there was no dnaQ49 strain which died out during such an operation. There was no plasmid in those cells whereby the resistance was shown to be due to mutation of genome gene.

TABLE 1

| Strain | 1st Run | | 2nd Run | | 3rd Run | | 4th Run | | 5th Run |
|---|---|---|---|---|---|---|---|---|---|
| (MNNG Concn) | AC | ID | AC | ID | AC | ID | AC | ID | AC |
| dnaQ49 | 30 | 8 | 300 | 6 | 1000 | 5 | 3000 | 16 | 6000 |
| Wild type (0) | 3 | 8 | 10 | 6 | 10 | 5 | 10 | 16 | 60 |
| Wild type (1) | 3 | 8 | 10 | 6 | 10 | 5 | 10 | 16 | 60 |
| Wild type (3) | 3 | 8 | 30 | 6 | 100 | 5 | 300 | 16 | d.o. |
| Wild type (6) | 3 | 8 | 6 | 6 | 10 | 5 | 10 | 16 | 30 |
| Wild type (10) | 6 | 8 | d.o. | | | | | | |
| Wild type (30) | 3 | 8 | d.o. | | | | | | |
| Wild type (60) | d.o. | | | | | | | | |

AC: Ampicillin Concentration;
IC: Incubated Days;
d.o.: died out

When the minimum growth inhibiting concentration (MIC) of various antibiotic substances to this ampicillin-resistant dnaQ49 strain was investigated, there was a strong resistance to cefotaxime which is a β-lactam antibiotic substance as same as ampicillin while no resistance was acquired for antibiotics having different action mechanisms from ampicillin (Table 2). Incidentally, the resistance concentration of ampicillin-resistant *Escherichia coli* which has been reported up to now is 1,500 µg/ml and the said resistance is due to plasmid. When mutagenesis was carried out at 37° C. without addition of ampicillin, it was not possible to obtain an ampicillin-resistant microorganism even by ten operations.

As a result, resistant microorganisms showing a resistance to ampicillin of high concentrations were able to be acquired within a short period as compared with the control using mutagen and the resistant microorganisms which were reported already. On the other hand, in the MNNG-treated group, extinction of the microorganism took place by a high-concentration treatment while, by a low-concentration treatment, resistant microorganism of 300 μg/ml was obtained only.

TABLE 2

|  | dnaQ | Wild-Type | Super-Amp-resistant dnaQ |
|---|---|---|---|
| Ampicillin | 2 | 1 | 2048 |
| Cefotaxime | 0.0313 | 0.0156 | 64 |
| Chloramphenicol | 1 | 0.5 | 0.5 |
| Tetracyctine | 0.25 | 0.25 | 0.25 |
| Rifampicin | 8 | 4 | 2 |
| Streptomycin | 1 | 1 | 0.5 |
| Nalidixic acid | 1 | 2 | 0.5 |
| Ofloxacin | 0.0156 | 0.0625 | 0.0156 |
|  | | Super-Stre.-resisting dnaQ | |
| Streptomycin | | 2048 | |
|  | | Super-Nali.-resisting dnaQ | |
| Nalidixic acid | | 2048 | |
|  | | Super-Oflo.-resisting dnaQ | |
| Ofloxacin | | 1024 | |

EXAMPLE 2

Mutation was introduced into dnaQ49 strain by the same way as in Example 1 to prepare drug-resistant microorganisms to each of ofloxacin, nalidixic acid and streptomycin. As a result, microorganisms resistant to 500 μg/ml of ofloxacin, to 7,000 μg/ml of nalidixic acid and to 26,000 μg/ml of streptomycin were obtained as shown in Tables 3–5.

TABLE 3

| Mutagenesis Treatment(s) for | Concentration of Ofloxacin (μg/ml) | Incubated Days |
|---|---|---|
| 1 time | 0.001 | 11 |
| 2 times | 0.01 | 6 |
| 3 times | 0.1 | 9 |
| 4 times | 1 | 4 |
| 5 times | 10 | 3 |
| 6 times | 30 | 3 |
| 7 times | 50 | 3 |
| 8 times | 60 | 3 |
| 9 times | 70 | 3 |
| 10 times | 80 | 3 |
| 11 times | 90 | 3 |
| 12 times | 100 | 7 |
| 13 times | 120 | 3 |
| 14 times | 132 | 3 |
| 15 times | 144 | 3 |
| 16 times | 150 | 7 |
| 17 times | 156 | 3 |
| 18 times | 168 | 2 |
| 19 times | 180 | 2 |
| 20 times | 210 | 2 |
| 21 times | 240 | 2 |
| 22 times | 270 | 2 |
| 23 times | 300 | 2 |
| 24 times | 320 | 6 |
| 25 times | 330 | 4 |
| 26 times | 340 | 4 |

TABLE 3-continued

| Mutagenesis Treatment(s) for | Concentration of Ofloxacin (μg/ml) | Incubated Days |
|---|---|---|
| 27 times | 350 | 3 |
| 28 times | 360 | 4 |
| 29 times | 370 | 3 |
| 30 times | 380 | 4 |
| 31 times | 400 | 2 |
| 32 times | 425 | 3 |
| 33 times | 450 | 3 |
| 34 times | 475 | 3 |
| 35 times | 500 | 3 |

*1) Incubation before the mutagenesis was carried out with 0.01 μg/ml of ofloxacin at 24° C. for 48 hours
*2) Under the mutagenesis condition, incubation was carried out at 37° C.
*3) dnaQ+ strain (wild type) did not grow in the presence of 0.1 μg/ml of ofloxacin.

TABLE 4

| Mutagenesis Treatment(s) for | Concentration of Nalidixic Acid (μg/ml) | Incubated Days |
|---|---|---|
| 1 time | 1 | 1 |
| 2 times | 10 | 1 |
| 3 times | 100 | 28 |
| 4 times | 200 | 2 |
| 5 times | 400 | 3 |
| 6 times | 600 | 2 |
| 7 times | 1000 | 2 |
| 8 times | 1100 | 1 |
| 9 times | 1200 | 1 |
| 10 times | 1300 | 1 |
| 11 times | 1400 | 1 |
| 12 times | 1600 | 1 |
| 13 times | 1800 | 2 |
| 14 times | 2000 | 1 |
| 15 times | 2500 | 1 |
| 16 times | 3000 | 1 |
| 17 times | 4000 | 1 |
| 18 times | 5000 | 9 |
| 19 times | 6000 | 5 |
| 20 times | 6200 | 11 |
| 21 times | 6400 | 7 |
| 22 times | 6600 | 5 |
| 23 times | 6800 | 5 |
| 24 times | 7000 | |

*1) Incubation before the mutagenesis was carried out with 1 μg/ml of nalidixic acid at 24° C. for 48 hours
*2) Under the mutagenesis condition, incubation was carried out at 37° C.
*3) dnaQ+ strain (wild type) did not grow in the presence of 10 μg/ml of nalidixic acid.

TABLE 5

| Mutagenesis Treatment(s) for | Concentration of Streptomycin (μg/ml) | Incubated Days |
|---|---|---|
| 1 time | 1 | 3 |
| 2 times | 10 | 1 |
| 3 times | 100 | 28 |
| 4 times | 1000 | 2 |
| 5 times | 3000 | 2 |
| 6 times | 4000 | 2 |
| 7 times | 6000 | 2 |
| 8 times | 8000 | 2 |
| 9 times | 9000 | 3 |
| 10 times | 10000 | 4 |
| 11 times | 12000 | 4 |
| 12 times | 14000 | 8 |
| 13 times | 16000 | 5 |
| 14 times | 17000 | 11 |
| 15 times | 18000 | 3 |
| 16 times | 19000 | 6 |
| 17 times | 20000 | 5 |

TABLE 5-continued

| Mutagenesis Treatment(s) for | Concentration of Streptomycin (µg/ml) | Incubated Days |
|---|---|---|
| 18 times | 21000 | 5 |
| 19 times | 22000 | 6 |
| 20 times | 23000 | 4 |
| 21 times | 24000 | 8 |
| 22 times | 25000 | 10 |
| 23 times | 26000 | |

*1) Incubation before the mutagenesis was carried out with 1 µg/ml of streptomycin at 24° C. for 48 hours
*2) Under the mutagenesis condition, incubation was carried out at 37° C.
*3) dnaQ+ strain (wild type) did not grow in the presence of 10 µg/ml of streptomycin.

In addition, when mutation of the enzyme relating to acquisition of resistance of microorganism was analyzed in the ofloxacin-resistant microorganism, serine at the position 83 of gyrase A was mutated to leucine in the microorganism having a low resistance (1–30 µg/ml). In the microorganism having a resistance degree of 100 µg/ml, serine at the position 83 of gyrase A was mutated to leucine and, in addition, serine at the position 80 of topoisomerase IV which is another enzyme necessary for increasing the resistance was mutated to arginine (Table 6). From that result, it has been shown that, according to the method of the present invention, an efficient mutagenesis is possible into plural genes. Further, the introduced mutation is the same as that of the resistant microorganism which is clinically observed and the mechanism for resistance acquisition where the fixed mutation increase together with an increase in resistant property was the same as well (J. Infect. Chemotherapy, 3:128–138, 1997).

The above result shows that the method of the present invention is able to simultaneously modify the plural genes relating to the expression of various biological functions and that such various modifications of gene can be utilized for prediction of appearance of new mutant such as drug-resistant microorganism and also for clarification of its mechanism, etc.

TABLE 6

| Degree of Resistance of Microorganism (OFLX) | GyrA | ParC |
|---|---|---|
| 0.1 µg/ml | no | no |
| 1.0 µg/ml | 83-Ser→Leu | no |
| 3.0 µg/ml | 83-Ser→Leu | no |
| 30.0 µg/ml | 83-Ser→Leu | no |
| 100.0 µg/ml | 83-Ser→Leu | 83-Ser→Arg |

EXAMPLE 3

Mutation was introduced into dnaQ49 strain by the same way as in Example 1 to prepare an alkali-resistant microorganism. The result is that, as shown in Table 7, a resistant microorganism up to pH 9.8 was obtained by mutagenesis for 12 times.

TABLE 7

| Mutagenesis Treatment(s) for | pH | Incubated Days |
|---|---|---|
| 1 time | 9.5 | 2 |
| 2 times | 9.4 | 2 |
| 3 times | 9.4 | 3 |

TABLE 7-continued

| Mutagenesis Treatment(s) for | pH | Incubated Days |
|---|---|---|
| 4 times | 9.4 | 2 |
| 5 times | 9.5 | 3 |
| 6 times | 9.5 | 2 |
| 7 times | 9.5 | 2 |
| 8 times | 9.7 | 39 |
| 9 times | 9.7 | 2 |
| 10 times | 9.7 | 3 |
| 11 times | 9.7 | 16 |
| 12 times | 9.8 | |

*1) Incubation before the mutagenesis was carried out at pH 9.5 and 24° C. for 48 hours
*2) Under the mutagenesis condition, incubation was carried out at 37° C.
*3) dnaQ+ strain (wild type) did not grow at pH 9.5.

EXAMPLE 4

It has been known that a codon "att" at the positions 4249–4251 of ampC gene of *Escherichia coli* (GenBank Accession No. J01611, J01583) is apt to be mutated to "ttt". Now, it was investigated whether the mutation of this site was caused by mutation of leading chain or by mutation of lagging chain.

1. Methods

Since it has been known that ampC gene of *E. coli* is synthesized as a lagging chain, a— chain plus addition sequence (SEQ ID NO:1) at the positions 4260–4212 was used as a probe for measuring the fidelity of lagging chain. In addition, a+ chain plus addition sequence (SEQ ID NO:2) at the positions 4235–4281 was used as a probe for measuring the fidelity of leading chain.

Further, an oligonucleotide of SEQ ID NO:3 was used as a linker DNA for measuring the fidelity of lagging chain and leading chain.

First, dnaQ49 was incubated at 37° C. for a period of one generation (time required for $OD_{550}$ of a microorganism suspension becomes two-fold) and then genomic DNA was purified and treated with restriction enzymes Fnu4HI and MspI to give a double-stranded DNA fragment (positions 4212–4279) including ampC genes.

The resulting DNA fragment was hybridized with a probe for measuring the fidelity of lagging chain and a linker DNA. Similarly, the DNA fragment was hybridized with a probe for measuring the fidelity of leading chain and a linker DNA.

The DNA fragment and the linker DNA hybridized with each probe were subjected to a ligation using T4 DNA ligase to purify the DNA followed by treating with a restriction enzyme TSPE I recognizing the "aatt".

After that, the DNA fragment hybridized with the probe for measuring the fidelity of lagging chain was subjected to a PCR amplification using each of an oligonucleotide having a base sequence (—chain of 4279–4259) of SEQ ID NO:4 and a linker DNA (SEQ ID NO:2) as a primer. In addition, the DNA fragment hybridized with the probe for measuring the fidelity of leading chain was subjected to a PCR amplification using each of an oligonucleotide having a base sequence of SEQ ID NO:5 and a linker DNA as primers.

Incidentally, as a control, mutation of lagging chain and leading chain was investigated by the same way for ampC gene of a wild type dnaQ+ strain as well.

2. Results

Figure 8:
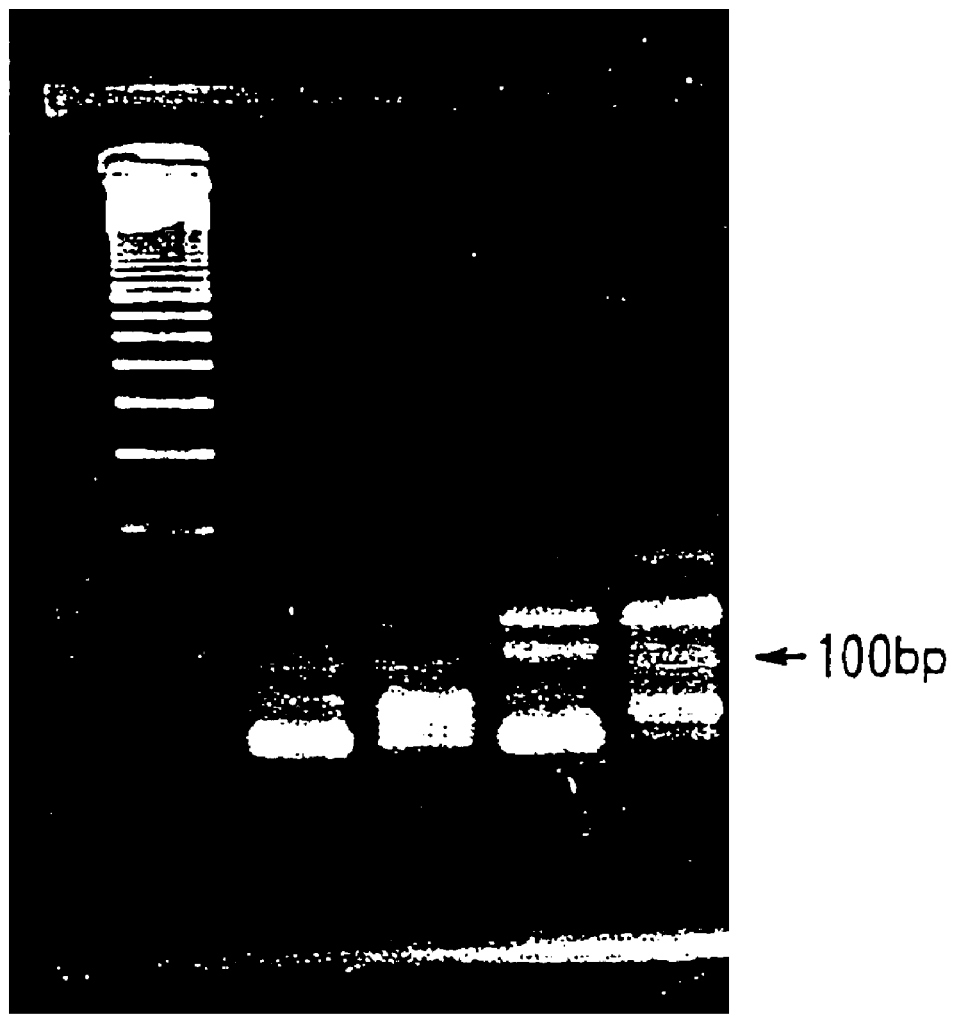
FIG. 8 is an agarose electrophoresis of DNA fragments derived from ampC genes from each of a wild type dnaQ$^+$ strain and a dnaQ49 strain.

Result of the PCR amplification is as shown in FIG. 8. The said FIG. 8 is a result of analysis of each PCR product by means of an agarose electrophoresis where lane 1 is the result of electrophoresis of the PCR product of a marker and lanes 2 and 3 are the results of electrophoresis of the PCR products of a DNA fragment derived from dnaQ+ strain ampC gene. As being obvious from the bands of the lanes 2 and 3, no band per 100 bp was observed in the DNA fragment (lane 2) hybridized with the probe for measuring the lagging chain and in the DNA fragment (lane 3) hybridized with the probe for measuring the leading chain. Such a fact means that, in the ampC gene of dnaQ+ strain, no mutation took place both in lagging chain and leading chain. Thus, the codon "att" was not mutated in any of the DNA fragments and, therefore, cleavage by the restriction enzyme TSPE I before the PCR took place whereby no PCR amplification was resulted.

On the other hand, lanes 4 and 5 are the result where the PCR products of DNA fragment derived from dnaQ49 strain ampC genes. As being obvious from the result shown in the lanes 4 and 5, no band showing the presence of a PCR product of 100 bp was observed in the DNA fragment (lane 5) hybridized with a probe for measuring the leading chain (i.e., no mutation took place in the leading chain) while, in the case of the DNA fragment (lane 4) hybridized with a probe for measuring the lagging chain, a band showing the presence of a PCR product of 100 bp was observed.

From the above result, it has been confirmed that, in the case of *Escherichia coli* dnaQ49 strain, much more mutations are accumulated in the lagging chain than in the leading chain even in the level of genomic DNA.

In accordance with the invention of this application, it is now possible to efficiently and effectively construct various useful mutants of microorganisms, cells or organism individuals. It is also now possible by analyzing the mutating conditions of the gene to clarify the mechanism of drug resistance, to estimate the occurrence of a novel insensible microorganism or to develop a drug therefor, to analyze the mutation of an oncogene and the mechanisms of cancer metastasis and increase in malignancy, to develop a therapeutic method using these mechanisms, etc.

What is claimed is:

1. A method for establishing a mutant of *Escherichia coli* dnaQ49 strain having tolerance to an antibiotic drug, wherein the tolerance is at least 1,000 times higher than that of wild type *Escherichia coli*, which comprises:

(a) introducing a mutation into the genomic DNA of *Escherichia coli* dnaQ49 strain by culturing it under a certain temperature;

(b) selecting a mutant *Escherichia coli* dnaQ49 strain tolerant to said drug; and (c) repeating said step (a) and said step (b) to develop increased tolerance of said mutant *Escherichia coli* dnaQ49 strain to said drug until the tolerance is at least 1,000 times higher than that of wild type *Escherichia coli*, wherein the repeating of said step (b) a second time and thereafter is carried out under a higher concentration of said drug than used in said step (b) therebefore, and wherein the repeating of said step (a) a second time and thereafter is carried out under the same concentration of said drug as used in said step (b) immediately therebefore.

2. A mutant of *Escherichia coli* dnaQ49 strain established by the method according to claim 1, which grows in the presence of 6,000 µg/ml of ampicillin.

3. A mutant of *Escherichia coli* dnaQ49 strain established by the method according to claim 1, which grows in the presence of 500 µg/ml of ofloxacin.

4. A mutant of *Escherichia coli* dnaQ49 strain established by the method according to claim 1, which grows in the presence of 7,000 µg/ml of nalidixic acid.

5. A mutant of *Escherichia coli* dnaQ49 strain established by the method according to claim 1, which grows in the presence of 26,000 µg/ml of streptomycin.

* * * * *